(12) United States Patent
Ciccone et al.

(10) Patent No.: US 7,766,920 B2
(45) Date of Patent: Aug. 3, 2010

(54) CANNULATED FASTENER SYSTEM

(75) Inventors: Paul Ciccone, Lincoln University, PA (US); Steven F Murray, Swarthmore, PA (US)

(73) Assignee: Synthes USA, LLC, West Chester, PA (US)

( * ) Notice: Subject to any disclaimer, the term of this patent is extended or adjusted under 35 U.S.C. 154(b) by 227 days.

(21) Appl. No.: 10/988,253

(22) Filed: Nov. 12, 2004

(65) Prior Publication Data

US 2005/0149031 A1    Jul. 7, 2005

Related U.S. Application Data

(60) Provisional application No. 60/524,880, filed on Nov. 26, 2003.

(51) Int. Cl.
*A61B 17/58* (2006.01)
(52) U.S. Cl. .................... 606/104; 606/86 B; 606/86 R
(58) Field of Classification Search ................. 606/72, 606/73, 99, 104, 300–320; 81/441, 451, 81/456, 457, 458, 177.4, 113
See application file for complete search history.

(56) References Cited

U.S. PATENT DOCUMENTS

| 126,366 | A | * | 4/1872 | Wills ........................ 411/387.4 |
| 848,194 | A | | 3/1907 | McMurtry |
| 851,181 | A | | 4/1907 | McMurtry |
| 868,436 | A | | 10/1907 | Hermand |
| 1,474,236 | A | * | 11/1923 | Byrne ........................ 81/124.1 |
| 1,503,692 | A | | 8/1924 | McCarthy |
| 1,537,929 | A | | 5/1925 | Lee |
| 1,539,736 | A | * | 5/1925 | Hearonemus ................ 81/457 |
| 1,543,175 | A | | 6/1925 | McCarthy |
| 1,714,045 | A | * | 5/1929 | Pratt ........................... 81/457 |
| 2,247,500 | A | | 7/1941 | Hutchison, Jr. |
| 2,256,012 | A | | 9/1941 | Blair |
| 2,277,945 | A | | 3/1942 | Ashleman |
| 2,366,448 | A | | 1/1945 | Greene et al. |
| 2,493,398 | A | | 1/1950 | Fricke |
| 2,506,835 | A | | 5/1950 | Johnson |
| 2,575,525 | A | | 11/1951 | Mitchell |
| 2,605,666 | A | | 8/1952 | Jorgensen et al. |
| 2,611,289 | A | | 9/1952 | Frank |
| 2,616,322 | A | | 11/1952 | Spreng |
| 2,659,255 | A | | 11/1953 | Bates |
| 2,811,883 | A | | 11/1957 | Cleaves |

(Continued)

FOREIGN PATENT DOCUMENTS

DE    3434807 A1    12/1985

(Continued)

*Primary Examiner*—Eduardo C Robert
*Assistant Examiner*—Tara R George
(74) *Attorney, Agent, or Firm*—Woodcock Washburn LLP

(57) ABSTRACT

A cannulated fastener system is provided for orthopedic applications that include attaching bone plates to bone. The bone fastener has a cannulation with an inner shape. One or more screwdrivers is provided with a shaft having a shape that matches the cannulation of the fastener to rotationally fix the fastener to the screwdriver. In addition, the screwdrivers have a cutting blade that begins the drilling of a hole for the bone fastener. The screwdrivers may either be for use with a single fastener or have multiple fasteners loaded within a retaining sleeve for automatic or controlled dispensing.

13 Claims, 10 Drawing Sheets

U.S. PATENT DOCUMENTS

| | | | |
|---|---|---|---|
| 2,820,383 A | 1/1958 | Red, Jr. | |
| 2,857,794 A | 10/1958 | Red, Jr. | |
| 2,868,053 A | 1/1959 | Jorgensen et al. | |
| 2,895,360 A | 7/1959 | Madsen | |
| 2,896,489 A | 7/1959 | Madsen | |
| 2,993,397 A | 7/1961 | Albertson et al. | |
| 3,005,367 A | 10/1961 | Vose | |
| 3,063,316 A | 11/1962 | Salierno | |
| 3,289,290 A | 12/1966 | Sandor | |
| 4,244,246 A | 1/1981 | Gillett | |
| 4,320,544 A * | 3/1982 | Bryant et al. | 7/158 |
| 4,507,817 A * | 4/1985 | Staffeld | 7/158 |
| 4,537,185 A * | 8/1985 | Stednitz | 606/73 |
| 4,581,962 A * | 4/1986 | Marbourg | 81/451 |
| 4,589,178 A | 5/1986 | Staffeld | |
| 4,760,844 A | 8/1988 | Kyle | |
| 4,878,794 A * | 11/1989 | Potucek | 411/395 |
| 4,884,572 A | 12/1989 | Bays et al. | |
| 4,895,148 A | 1/1990 | Bays et al. | |
| 4,924,865 A | 5/1990 | Bays et al. | |
| 4,927,421 A | 5/1990 | Goble et al. | |
| 4,950,270 A | 8/1990 | Bowman et al. | |
| 4,976,715 A | 12/1990 | Bays et al. | |
| 5,059,206 A * | 10/1991 | Winters | 606/213 |
| 5,098,435 A * | 3/1992 | Stednitz et al. | 606/73 |
| 5,129,901 A | 7/1992 | Decoste | |
| 5,139,499 A * | 8/1992 | Small et al. | 606/73 |
| 5,152,764 A | 10/1992 | Goble | |
| 5,203,784 A * | 4/1993 | Ross et al. | 606/104 |
| 5,207,545 A * | 5/1993 | Kochanski | 411/383 |
| 5,211,647 A | 5/1993 | Schmieding | |
| 5,249,489 A | 10/1993 | Weisman | |
| 5,255,485 A * | 10/1993 | Lemke et al. | 52/410 |
| 5,308,203 A | 5/1994 | McSherry et al. | |
| 5,334,204 A | 8/1994 | Clewett et al. | |
| 5,354,299 A * | 10/1994 | Coleman | 606/73 |
| RE34,871 E | 3/1995 | McGuire et al. | |
| 5,403,137 A | 4/1995 | Grün et al. | |
| 5,437,211 A | 8/1995 | Wolfe | |
| 5,549,431 A | 8/1996 | Royle | |
| 5,551,321 A | 9/1996 | Bottiglieri | |
| 5,569,252 A | 10/1996 | Justin et al. | |
| 5,590,574 A | 1/1997 | Lide | |
| 5,601,562 A | 2/1997 | Wolf et al. | |
| 5,640,889 A | 6/1997 | Anderson | |
| 5,645,547 A | 7/1997 | Coleman | |
| 5,695,497 A | 12/1997 | Stahelin | |
| 5,730,744 A | 3/1998 | Justin et al. | |
| 5,735,854 A | 4/1998 | Caron et al. | |
| 5,741,268 A | 4/1998 | Schütz | |
| 5,833,415 A * | 11/1998 | McSherry | 411/31 |
| 5,899,906 A | 5/1999 | Schenk | |
| 5,904,685 A | 5/1999 | Walawalkar | |
| 5,968,045 A | 10/1999 | Frazier | |
| 5,968,046 A | 10/1999 | Castleman | |
| 5,997,541 A | 12/1999 | Schenk | |
| 6,004,321 A | 12/1999 | Graser | |
| 6,010,513 A * | 1/2000 | Tormala et al. | 606/142 |
| 6,030,162 A * | 2/2000 | Huebner | 411/413 |
| 6,032,557 A * | 3/2000 | Anderson | 81/451 |
| 6,048,344 A | 4/2000 | Schenk | |
| 6,096,060 A | 8/2000 | Fitts et al. | |
| 6,165,203 A | 12/2000 | Krebs | |
| 6,179,840 B1 | 1/2001 | Bowman | |
| 6,273,890 B1 | 8/2001 | Frazier | |
| 6,283,973 B1 | 9/2001 | Hubbard et al. | |
| 6,306,140 B1 | 10/2001 | Siddiqui | |
| 6,319,252 B1 * | 11/2001 | McDevitt et al. | 606/60 |
| 6,328,746 B1 | 12/2001 | Gambale | |
| 6,364,884 B1 | 4/2002 | Bowman et al. | |
| 6,402,757 B1 | 6/2002 | Moore, III et al. | |
| 6,402,766 B2 | 6/2002 | Bowman et al. | |
| 6,423,073 B2 | 7/2002 | Bowman | |
| 6,436,100 B1 * | 8/2002 | Berger | 606/73 |
| 6,436,110 B2 | 8/2002 | Bowman et al. | |
| 6,447,517 B1 | 9/2002 | Bowman | |
| 6,468,277 B1 | 10/2002 | Justin et al. | |
| 6,497,707 B1 | 12/2002 | Bowman et al. | |
| 6,527,777 B2 | 3/2003 | Justin | |
| 6,533,454 B1 * | 3/2003 | Kaikkonen et al. | 378/205 |
| 6,544,281 B2 | 4/2003 | ElAttrache et al. | |
| 6,554,852 B1 | 4/2003 | Oberlander | |
| 6,557,727 B1 | 5/2003 | Robertson | |
| 6,616,665 B2 | 9/2003 | Grafton et al. | |
| 6,629,977 B1 | 10/2003 | Wolf | |
| 6,634,261 B1 | 10/2003 | Griffin | |
| 6,673,094 B1 * | 1/2004 | McDevitt et al. | 606/232 |
| 7,074,203 B1 * | 7/2006 | Johanson et al. | 602/72 |
| 2001/0027322 A1 | 10/2001 | Bowman | |
| 2001/0037113 A1 | 11/2001 | Justin | |
| 2002/0013608 A1 | 1/2002 | ElAttrache et al. | |
| 2002/0049447 A1 * | 4/2002 | Li | 606/73 |
| 2002/0052628 A1 | 5/2002 | Bowman | |
| 2002/0169453 A1 | 11/2002 | Berger | |
| 2002/0183751 A1 | 12/2002 | Justin et al. | |
| 2003/0028193 A1 | 2/2003 | Weil et al. | |
| 2003/0069582 A1 | 4/2003 | Culbert | |
| 2003/0078585 A1 | 4/2003 | Johnson et al. | |
| 2003/0120277 A1 | 6/2003 | Berger | |
| 2003/0125749 A1 | 7/2003 | Yuan et al. | |
| 2003/0125750 A1 | 7/2003 | Zwirnmann et al. | |
| 2004/0243139 A1 * | 12/2004 | Lewis et al. | 606/104 |

FOREIGN PATENT DOCUMENTS

| | | |
|---|---|---|
| EP | 0 674880 A1 | 10/1995 |
| EP | 0 674880 B1 | 12/1996 |
| JP | 5060119 A | 3/1993 |
| JP | 8071083 A | 3/1996 |

* cited by examiner

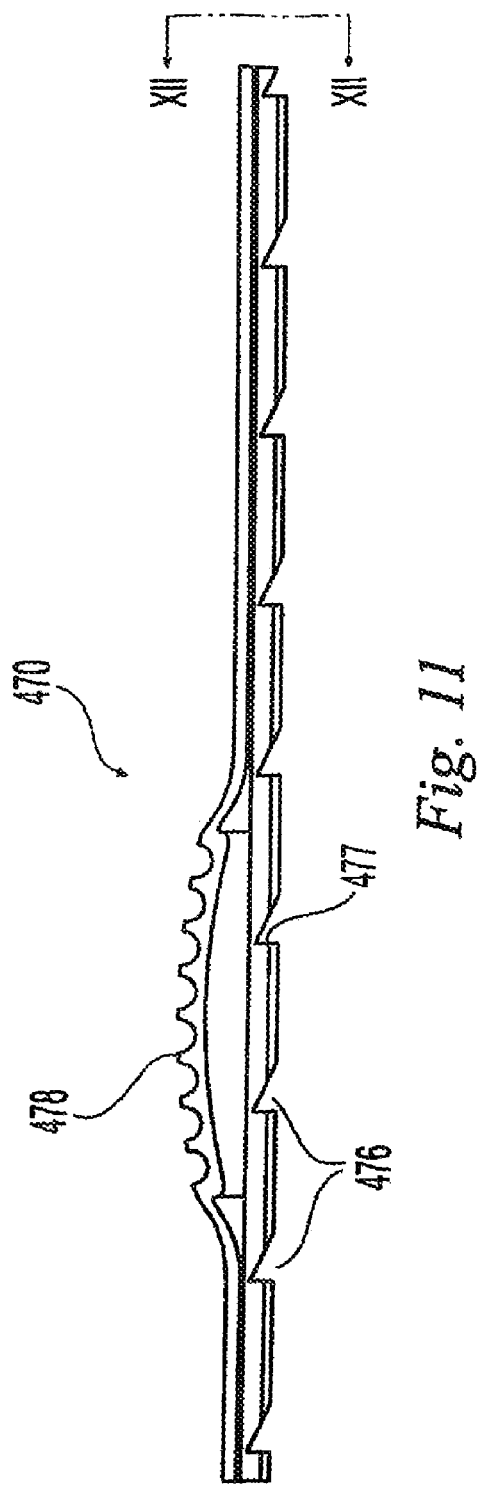
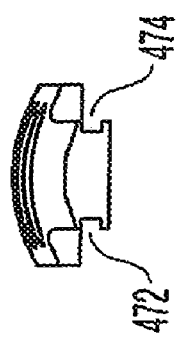

CANNULATED FASTENER SYSTEM

CROSS REFERENCE TO RELATED APPLICATIONS

The present application claims the benefit under 35 U.S.C. §119(e) of U.S. Provisional Patent Application No. 60/524,880, filed Nov. 26, 2003, the entirety of which application is expressly incorporated herein by reference thereto.

FIELD OF THE INVENTION

The present invention relates generally to a cannulated screw system for use in orthopedic surgery. More particularly, the present invention relates to a cannulated screw through which a blade may be inserted for drilling a screw hole in advance of the screw and which may also be used to rotate the screw to insert it into bone. The blade may be configured to hold a single screw or to allow the stacking of multiple screws for sequential drilling and insertion of multiple screws. In either blade configuration the tool is provided with a cutting blade and a polygonal shaft section matching the shape of at least a portion of the cannulation of the screw to allow the screw to be rotated using the tool.

BACKGROUND OF THE INVENTION

The present invention relates generally to a cannulated screw system for use in orthopedic surgery. Bone screws are generally installed after a screw hole has been separately drilled. As such, current systems generally require separate hole drilling and screw driving instruments. Furthermore, bone screws used, for example, in maxillofacial applications are typically small and may be difficult to manipulate during installation. Thus, there is a concern in using such small screws in that they may be lost during surgery or may fall into the surgical site. The present invention allows a surgeon to simultaneously drill a screw hole and install a bone screw using a single device. In addition, the present invention allows a surgeon to preload multiple screws onto a screwdriver so that he can quickly manipulate and install multiple screws without removing the screwdriver from the incision area. The preloading of the screws is especially advantageous with the small bone screws used in maxillofacial surgery because it eliminates the need for the surgeon to manipulate multiple small screws on an individual basis, thus reducing the amount of user attention required to interface the screws with the instrument. The screw installation procedure may therefore be performed faster and safer, benefiting both surgeon and patient.

SUMMARY OF THE INVENTION

The invention relates to a cannulated screw system used in orthopedic surgery. The screw has threads on the outer diameter of the shaft for insertion into bone, with the tip of the screw preferably having multiple cutting flutes. The head region of the screw may have a head consisting mainly of a flange. A polygonal cannulation extends through at least a portion of the length of the shaft and optional head to receive a driving torque from a screwdriver for inserting the screw into a bone.

The cannulated screw system may include a screwdriver configured to hold a single screw and/or a multiple screw screwdriver in which screws are stacked and sequentially dispensed. All configurations of the screwdriver may include a flat blade portion at the distal tip to cut the bone surface to initiate engagement of the screw, and a polygonal section behind the flat blade portion to match the polygonal portion of the cannulation of the screw. All configurations of the screwdriver may also include a polygonal socket or polygonal outer surface at the proximal end to engage a driver.

One embodiment of a multiple screw screwdriver features spring-advance of the screws as they are inserted into the bone. The spring-advance multiple screw screwdriver may have a screwdriver shaft with an extended polygonal shaft section behind the flat blade portion to hold multiple screws, a coil spring, and a retaining sleeve may be transparent. The retaining sleeve surrounds the screwdriver shaft, with the screws surrounding the screwdriver shaft and occupying the annular space between the screwdriver shaft and retaining sleeve. The coil spring occupies the annular region between the polygonal shaft section and the retaining sleeve, and may also rest between a shoulder on the screwdriver shaft and the flange of the most proximal screw in a stack of screws on the polygonal shaft section. The distal end of the retaining sleeve may have a lip that retains the screws until adequate force is exerted to separate portions of the distal end of the retaining sleeve separated by slots. The coil spring biases the screws such that when one screw is dispensed from the distal end of the retaining sleeve, the shaft of the following screw protrudes from the retaining sleeve. The lip at the distal end of the retaining sleeve may prevent the flange of the following screw from exiting the retaining sleeve until the screw is inserted into bone sufficiently to exert a force sufficient to pull the screw from the retaining sleeve.

The spring-advance multiple screw screwdriver may be loaded with screws by sliding over the drilling tip a tube of a diameter that will fit inside the cannulation of the screws. The screws may then be placed over the tube and onto the extended polygonal shaft section against the coil spring. The retaining sleeve is then placed over the tube/shaft/screws and screwed or snapped onto the screwdriver shaft, depressing the coil spring and forcing the screws off the tube and onto the screwdriver shaft. The tube is then removed from the drilling tip.

A second embodiment of a multiple screw screwdriver features ratchet-advance of the screws. The ratchet-advance multiple screw screwdriver may have a screwdriver shaft with an extended polygonal shaft section behind the flat blade portion to hold multiple screws, a plunger, a retaining sleeve, and a ratchet slide. As with the spring-advance multiple screw screwdriver, the screws of the ratchet-advance multiple screw screwdriver may occupy the annular space between the extended polygonal shaft section and the sleeve. The retaining sleeve may have a series of evenly spaced depressions in the shape of a right triangle on the inner surface of the sleeve and, directly opposed to those depressions, an elongated rectangular slot. The ratchet slide may have a series of depressions of identical shape and spacing to the depressions of the retaining sleeve. The ratchet slide may be sized and may have grooves on either side that allow it to slide within the elongated groove of the retaining sleeve. Alternatively, the retaining sleeve may have grooves on either side of the elongated slot within which may slide the sides of the ratchet slide. The plunger is a cylinder which may be sized to occupy the annular space between the extended polygonal shaft section and the sleeve on the proximal side of the loaded screws, and may have two opposed legs extending from the cylinder, the ends of which may each have a single tab shaped to mesh with the right triangle shaped depressions of the retaining sleeve and the ratchet slide. Advance of loaded screws may be accomplished by sliding the ratchet slide within the elongated groove of the sleeve in the distal direction. The right angle side of one of the depressions in the ratchet slide may engage the matching tab of one of the plunger legs and force the plunger to move with the ratchet slide. However, the tab on the opposite side leg may move out of the depression in the sleeve due to the acute angle of the mating surfaces forcing the leg toward the center of the retaining sleeve, allowing the plunger to slide within the retaining sleeve. When the ratchet slide is returned to the proximal end of the elongated slot, the relative motion between the tabs on the legs of the plunger and depressions in the retaining sleeve and ratchet slide is reversed, causing the plunger to remain in place within the sleeve. This ratcheting motion may force the plunger to advance the screws by applying a force between the plunger and the upper flange of the screw contacted by the lower surface of the plunger.

The ratchet-advance multiple screw screwdriver may be loaded by sliding the plunger onto the extended polygonal shaft section followed by the screws. The retaining sleeve—with the ratchet slide already mounted—is then slid over the screws and plunger (with the legs and tabs of the plunger aligned with the triangular depressions in the retaining sleeve and ratchet slide) and snapped into place. The retaining sleeve, the screwdriver shaft, and the plunger may all be keyed to ensure that the legs of the plunger align with the depressions of the retaining sleeve and ratchet slide upon assembly.

In any embodiment of the screwdriver, one or more screws may be loaded onto the shaft of the screwdriver. The flat blade portion of the screwdriver may have a point and cutting edges that are applied to the bone surface. As the screwdriver is rotated and axial pressure is applied, the flat blade portion bores into the bone surface, with the cutting flutes of the screw beginning to also cut into the bone surface once the flat blade portion of the screwdriver shaft is at a sufficient depth, and the self-tapping threads of the screw eventually engaging the bone. As the screw enters the bone, it eventually pulls free of the screwdriver blade and—in the case of the multiple screw screwdrivers—free of the retaining sleeve. This allows the following screw to be advanced in the multiple screw screwdrivers.

The screwdriver shaft may be fabricated from surgical steel or similar material suitable for cutting bone. The coil spring may be fabricated from spring steel or any other suitable spring material. The retaining sleeves, plunger, and ratchet slide are preferably made of a polymer, although other materials are possible.

BRIEF DESCRIPTION OF THE DRAWINGS

Preferred features of the present invention are disclosed in the accompanying drawings, wherein:

FIG. 11 is a side view of a ratchet slide of the multiple screw screwdriver of FIG. 9;

FIG. 12 is an end view of the ratchet slide of the multiple screw screwdriver of FIG. 9;

DETAILED DESCRIPTION OF THE PREFERRED EMBODIMENTS

Figure 1A:
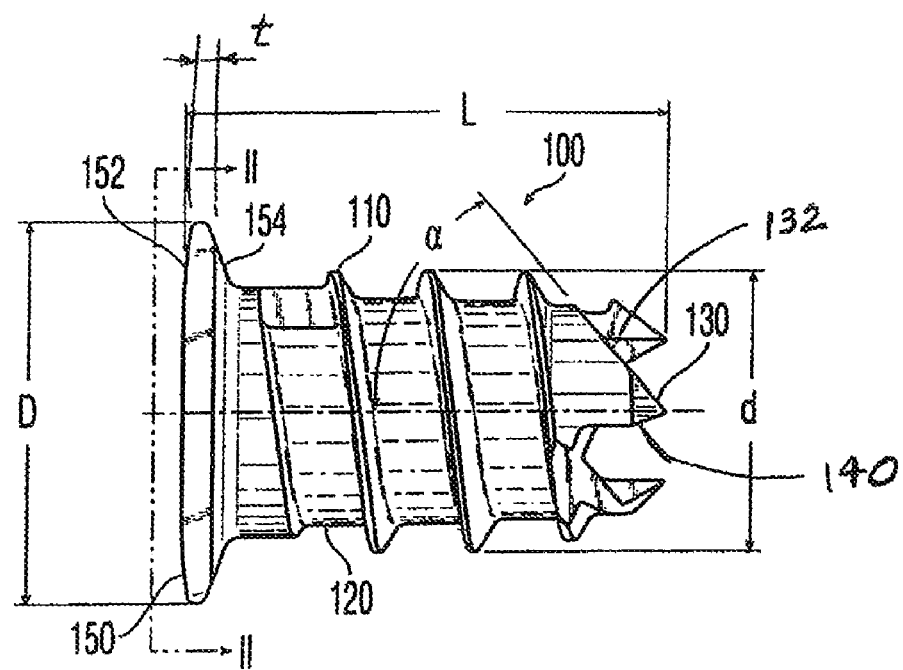
FIG. 1a is a side view of an exemplary screw of the present invention.
Figure 2:
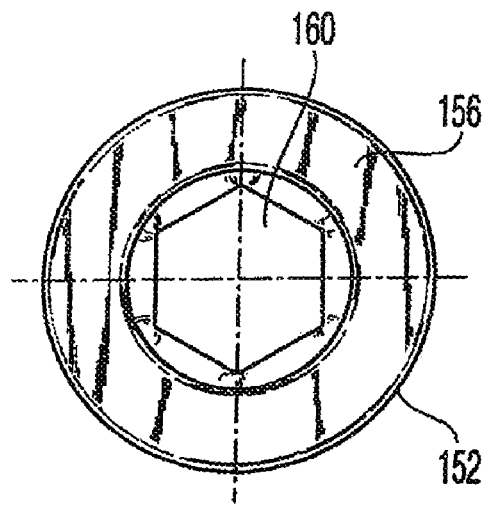
FIG. 2 is an end view of the screw of FIG. 1.

Referring to FIGS. 1a and 2, there is shown an exemplary bone screw 100. Bone screws of this type may be used in a variety of orthopedic applications, such as to attach bone plates to fractured bone segments of the jaw or face to hold the bone segments in a desired relative position during healing. When used in maxillofacial applications, the bone plates and screws may be designed to have a "low profile" to minimize any aesthetic impact on the patient's appearance during the healing process.

Bone screw 100 may comprise threads 110 on the outer diameter of the shaft 120, a tip 130, and a head region 150. Tip 130 may have one or more cutting flutes 140 suitable for cutting into bone. Head region 150 may further comprise a flange 152 for seating the screw 100 on a bone or bone plate surface. The flange 152 may have an upper side surface 156 and an underside surface 154. The upper side surface 156 may be substantially flat, forming a plane substantially perpendicular to the longitudinal axis of the shaft 120. The underside surface 154 of flange 152 may likewise be substantially flat (i.e., parallel to the plane of the upper side surface 156) or it may be sloped toward the shaft so as to be non-orthogonal with respect to the screw shaft axis and non-parallel to the plane of the upper side surface 156. Alternatively, the underside surface 154 may be spherically shaped so as to conform to spherical bone screw holes formed in an associated bone plate. In one embodiment, the thickness "t" may be from about 0.2 millimeters (mm) to about 6.0 mm. For the embodiment of the screw having a sloped underside surface 154, the head flange 152 thickness "t" may vary (i.e., it may be thinner near the outer circumference of the flange and thicker near the shaft 120). In addition, screw 100 may have a locking head comprising a conically threaded section.

Figure 1B:
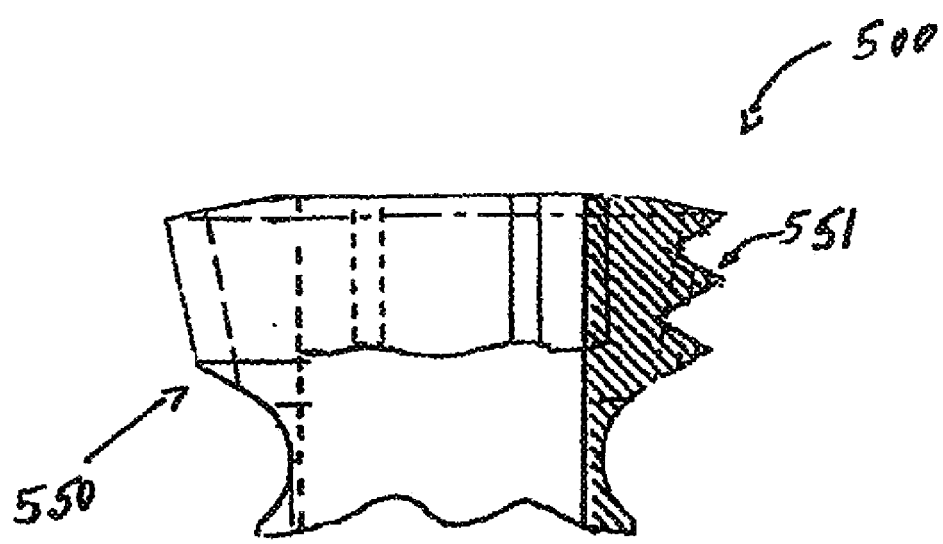
FIG. 1b is a side view of a locking head design for the screw of the present invention.

FIG. 1b shows an alternative embodiment in which screws 500 may be used in conjunction with a bone plate having threaded bone screw holes. The screws of this embodiment may have a head region 550 comprising threads configured to engage the threads disposed within the plate hole, to lock the screws to the plate. In the illustrated embodiment, screw 500 has a locking head comprising conical threads which are configured to mate with corresponding conical threads of a bone plate. The screws 500 of this embodiment may alternatively be provided with spherical threaded head sections, configured to engage corresponding spherical threads of the bone plate. When screws having threaded head regions are provided, the pitch of such threads may match the pitch of the threads in the body of the screw, such that the rate of advancement of the engagement of the screw into the plate may be the same as the rate of advancement of the screw body into the bone.

A polygonal cannulation 160 may extend through at least a portion of the length of the shaft 120 to allow insertion of a tool for transmitting driving torque so that screw 100 may be driven into a bone. In the illustrated embodiment, cannulation 160 comprises a hexagonal cross-section, however, any appropriate polygonal cannulation may be provided. Likewise, a non-polygonal cannulation may be provided, or a cannulation having any variety of ridges, grooves, notches, etc., appropriate for engaging corresponding surface features of a driving element to rotationally fix the screw relative to the driving element. The screw 100 may further comprise a length "L", which may be selected in the range of from about 2 mm to about 60 mm, an outside screw diameter "d", which may be selected in the range of from about 1.5 mm to about 5.0 mm, and a flange diameter "D", which may be selected in the range of from about 2.0 mm to about 6.0 mm.

Screw 100 may have a tip 130 with a plurality of cutting flutes 140, each flute 140 having a trailing edge 132 oriented at an angle α with respect to the longitudinal axis of the screw. In one embodiment, α may be selected in the range from about 35° to about 70°. In an exemplary embodiment, α may be approximately 50°. The advantage of selecting a trailing edge angle in the aforementioned range is that it permits a reasonably sized cutting flute without removing too much thread surface from the screw, which could reduce pullout strength of the screw from the bone. Threads 110 may have a pitch selected in the range of from about 0.15 mm to about 2.0 mm. In an alternative embodiment, thread height may be selected in the range of about 0.1 mm to about 0.75 mm. Screws having thread angles, thread pitches, and thread heights different from those identified herein may also be provided, as will be apparent to one of ordinary skill in the art.

Threads 110 may be self-tapping, and in an alternative embodiment, the screw 100 may also be self-drilling. The cannulated screws 100 may be in various materials, such as stainless steel, titanium, polymer, or bioresorbable materials. Furthermore, the invention is not limited to cannulated screws, but may include other appropriate cannulated bone fasteners such as bone tacks, rivets, etc. Where bone tacks, rivets or other bone fasteners are used they may be provided in a variety of materials such as metals (e.g., stainless steel or titanium), polymer, or bioresorbable materials.

Head region 152 may have a thickness "t" that is very small, owing to the fact that most of the torque from the screwdriver may be transmitted to screw 100 via the cannulation in the shaft. This is different from typical bone fasteners in which the screwdriver engaging surface is located almost entirely within the head of the fastener, thus requiring a substantial head thickness to provide corresponding high strength. The cannulated shaft arrangement of the present invention eliminates the need for such a large head, and as a result, flange 152 of head region 150 may have a very low profile. Such a low profile fastener may be particularly advantageous in applications where there is little muscle or other tissue situated between the screw and/or bone plate and the patient's skin, such as in maxillofacial applications where bone plates are often installed subcutaneously in prominent regions of the face. Bone screws having normal head profiles may protrude significantly from the top of the associated bone plate, thus resulting in a visible bump or discontinuity in the skin. The thin head profile of screw 100, however, may protrude only slightly, or not at all, from the top surface of the bone plate, thus providing no significant additional discontinuity in the patient's facial features. Nevertheless, a low head profile is not critical to the success of the present invention, and screws having any head profile known in the art may be used in accordance with the desires of the installing surgeon.

It should be noted that the invention is not limited to screws for use in maxillofacial applications, but may cover any appropriate screws or other fasteners used in other orthopedic applications. Such screws or fasteners may have dimensions greater than those specifically identified herein.

Figure 3:
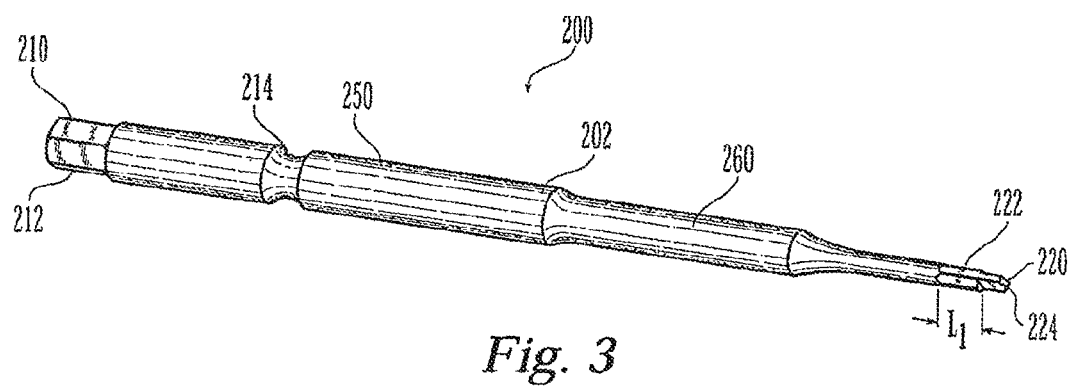
FIG. 3 is a perspective view of a single screw screwdriver.

Referring to FIG. 3, single screw screwdriver 200 may have a proximal end 210, a distal end 220, and a shaft portion 202. Proximal end 210 may have a tool engaging portion 212 for coupling with the female coupling of an external driving tool such as a hand or power driver. Tool engaging portion 212 may alternatively comprise a socket for receiving the male end of a drive tool. A driver retention groove 214 may be provided in shaft portion 202 adjacent the tool engaging portion 212 to accommodate a standard ball detent mechanism which may be provided with typical drive tools.

Figure 4:
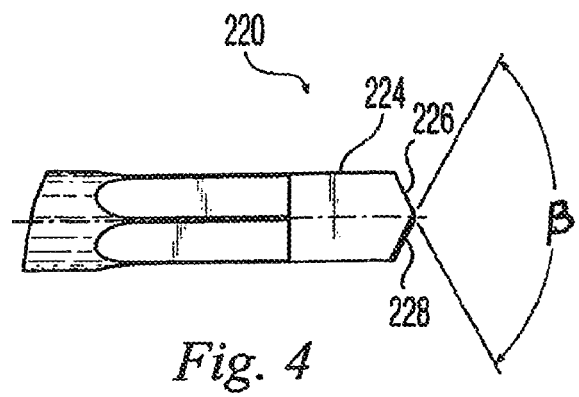
FIG. 4 is a detail view of the tip of the single screw screwdriver of FIG. 3.
Figure 5A:
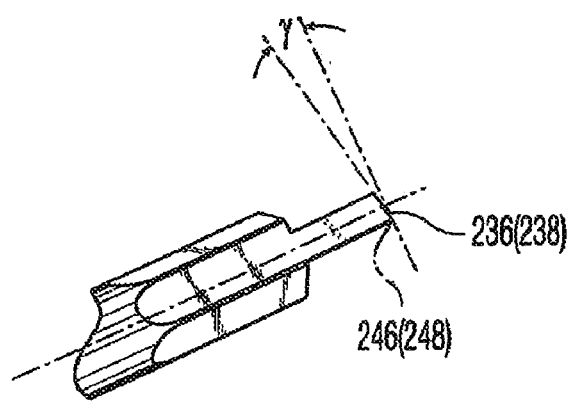
FIG. 5a is a side view of the detail of the tip shown in FIG. 4.
Figure 5B:
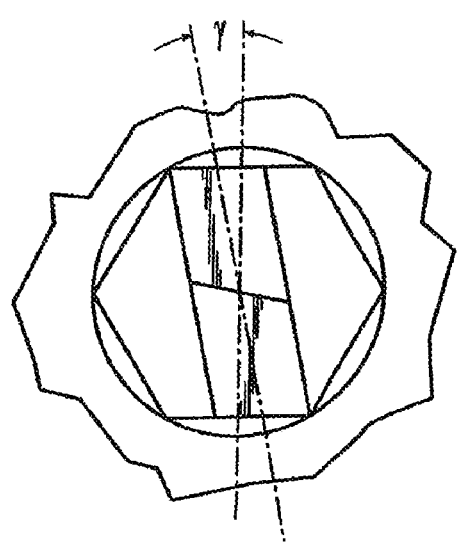
FIG. 5b is an end view of the tip shown in FIG. 4.

Distal end 220 may comprise a polygonal shaft 222 of length "$L_1$" and a drilling tip 224 which may extend past the distal end of screw 100 by a distance of from about 0.5 mm to about 10.0 mm past the distal end of screw 100. Length $L_1$ may be selected in the range of from about 2 mm to about 60 mm. In one embodiment, length $L_1$ may be about 30 mm. Drilling tip 224 may be flat with a pointed end 225 to facilitate cutting into bone. Polygonal shaft 222 may be of a shape configured to match the cannulation 160 of screw 100. As with cannulation 160 of screw 100, polygonal shaft 222 is shown as having a hexagonal cross-section, although other polygonal shapes may be used, as previously described. FIGS. 4 and 5 show details of distal end 220 of single screw screwdriver 200. In the illustrated embodiment, drilling tip 224 has two opposed blade portions 226, 228 having cutting surfaces that, when viewed from the side, form an included angle β. Included angle β may be selected in the range of from about 90° to about 160°. In an exemplary embodiment, β is approximately 130°. Blade portions 226, 228 also may have faces 236, 238 that, when viewed from the top (as shown in FIG. 5b), may be inclined at an angle γ with respect to leading edges 246, 248. In one embodiment, γ may be selected in the range of from about 5° to about 30°. In an exemplary embodiment, angle γ may be approximately 10°. Drilling tips also may be provided having angles β and γ different from those identified herein, as will be apparent to one of ordinary skill in the art. It is also noted that any appropriate drilling tip design known in the art may be used to provide the desired cutting into bone.

In an alternative embodiment, a screwdriver may be provided without a drilling tip, such that the distal end of the screwdriver may not extend past the tip of the screw when the screw is fit onto the screwdriver. In such a case, a pilot hole may be drilled into bone using traditional methods (e.g., awl, tap, etc.), and the screwdriver with cannulated screw may be used to drive the screw into the bone. Such a configuration may be advantageous when large sized screws are used.

The shaft portion 202 of the screwdriver 200 may be provided with at least two different diameter sections 250, 260, with the smallest diameter section 260 provided adjacent the distal end to increase visibility of the surgical working space. Larger diameter section 250 may be approximately 3.15 mm in diameter and may have a length of approximately 27 mm, while smaller diameter section 260 may have a diameter selected in the range of from about 1.2 mm to about 2.5 mm, and a length of approximately 10 mm. Again, these dimensions should be considered as representative only and are not critical to the invention. It is further noted that although increased visibility of the surgical working space is a benefit, the selected reduced diameters should not be so small as to compromise the structural integrity and rigidity of the screwdriver.

Figure 6:
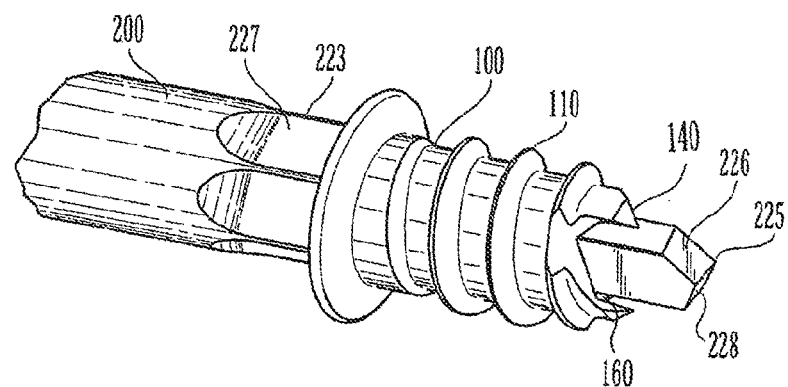
FIG. 6 is a perspective view of the screw of FIG. 1 on the single screw screwdriver of FIG. 3.

FIG. 6 shows screw 100 installed on distal end 220 of single screw screwdriver 200. Polygonal shaft 222 (hidden by screw) may engage cannulation 160, thus enabling screwdriver 200 and screw 100 to rotate together. The proximal end 223 of polygonal shaft 222 may comprise a flared portion 227 which may interact with the head flange 152 and cannulation 160 of screw 100 to maintain screw 100 on the screwdriver. Thus, the cannulation of screw 100 may wedge against the flared portion 227, causing an interference between the surfaces that may provisionally lock them axially together. Once the screw 100 is fit to the screwdriver 200, pointed end 225 of screwdriver 200, which extends distally beyond the end of the screw 100, may be applied to the surface of a targeted bone area and rotated. The rotation of blade portions 226, 228 against the bone along with the application of axial force, results in a cutting of the bone accompanied by an axial advance of screwdriver 200 along with screw 100 into the bone. When the hole in the bone reaches a depth sufficient for the screw 100 to engage the bone, cutting flutes 140 of screw 100 may engage the bone surface and enlarge the diameter of the hole in the bone. Self-tapping threads 110 may then engage the bone and the bone screw 100 may continue to advance as the screw is rotated. It is noted that this advancement may continue irrespective of any further axial movement of the screwdriver, owing to the self-tapping nature of the threads which, when the screw is rotated, may cause the screw to drive itself down into the drilled hole. Thus, full seating of the screw in bone may be achieved by holding the screwdriver axially fixed as it rotates and allowing the screw to translate along the hex surface as it tunnels into the bone. When screw 100 is driven into the bone to the desired depth, screwdriver 200 can be removed by pulling it axially out and away from polygonal cannulation 160 of bone screw 100. Thereafter, another screw may be applied to distal end 220 of screwdriver 200 for subsequent drilling and insertion.

Figure 7:
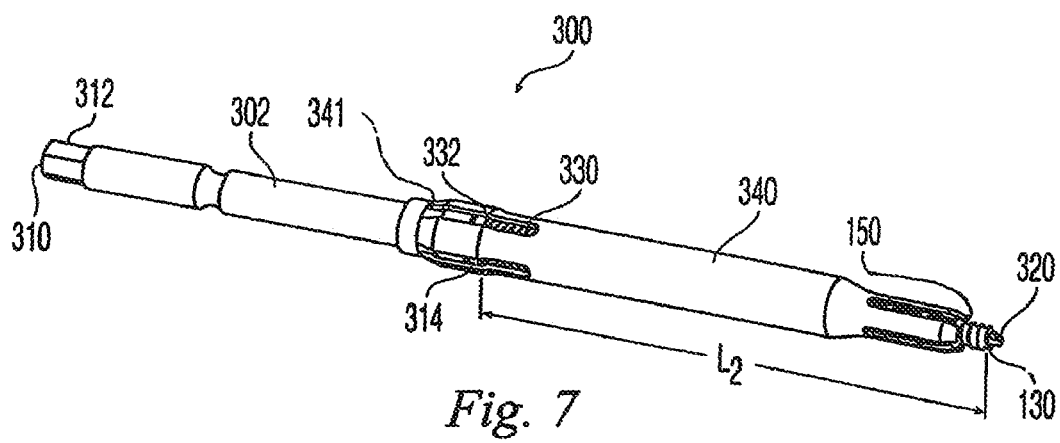
FIG. 7 is a perspective view of spring-advance multiple screw screwdriver.
Figure 8:
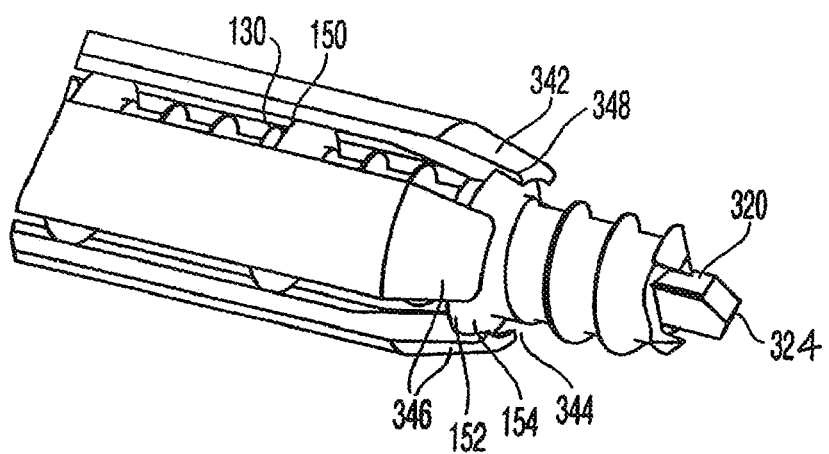
FIG. 8 is a detail view of the distal end of the spring-advance multiple screw screwdriver of FIG. 7.
Figure 9:
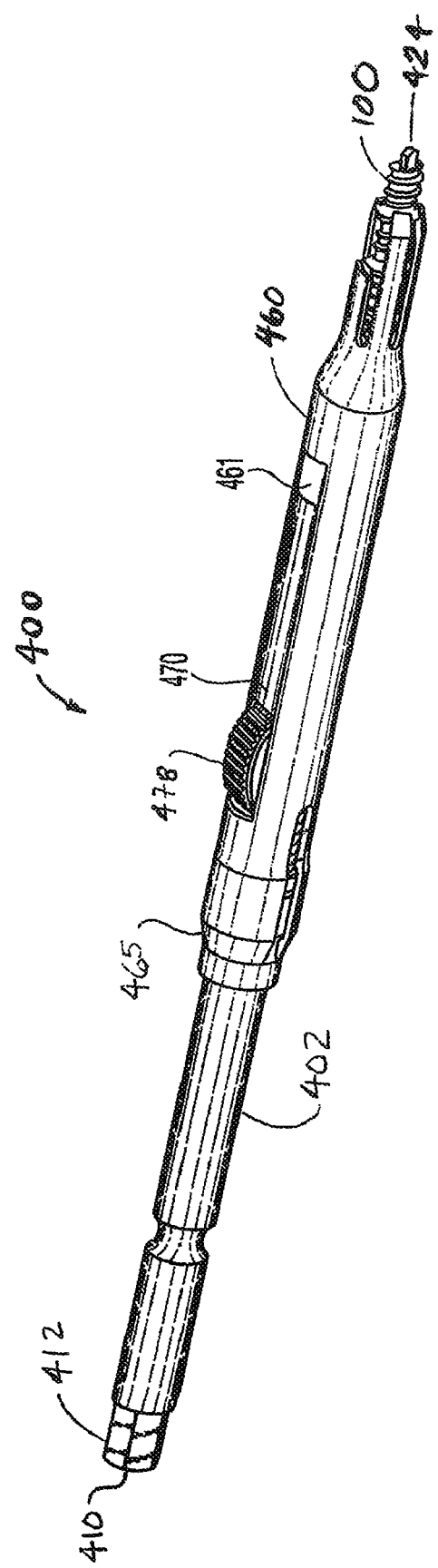
FIG. 9 is a perspective view of a ratchet-advance multiple screw screwdriver.

FIGS. 7 and 8 show a spring-advance multiple screw screwdriver 300 in which multiple screws may be pre-loaded on the screwdriver and may be advanced automatically to along the screwdriver for sequential insertion at a surgical site. Screwdriver 300 may comprise a stacked screwdriver shaft 302, a spring element 330, and a transparent screw retaining sleeve 340 having a proximal end 341 configured to receive the stacked screwdriver shaft 302. The retaining sleeve 340 may extend from the proximal section of the screwdriver shaft 302 to near the distal end 320, thereby covering the shaft portion, spring and screws. The distal end 342 of the retaining sleeve 340 may be configured to provisionally engage the first screw 100 in line, thus preventing the screws 100 in the stack from prematurely disengaging from the end of the screwdriver shaft 302. Retaining sleeve 340 is depicted as being transparent to allow a user to determine the number of screws 100 loaded into the screwdriver 300, however, it is not necessary that the screw retaining sleeve 340 be transparent. Where a non-transparent retaining sleeve 340 is provided, other configurations of the sleeve 340 may be provided to allow the user to determine the number of screws remaining on the shaft. Such alternative configurations could comprise a coloring system in which screws are provided in different colors, the colors indicative of the number of screws remaining. Alternatively, a slot may be provided along the length of the retaining sleeve 340 such that a portion of each screw may be visible to the user. Other similar stack-visualization arrangements may likewise be implemented, as will be apparent to one of ordinary skill in the art.

Retaining sleeve 340 may be fabricated from a polymer and can be retained on stacked screw driver blade 302 using a snap-fit or threading, or the sleeve may be fused onto the screwdriver shaft in halves, or any number of other retention arrangements that are well-known in the art.

The screwdriver shaft may be made of surgical steel or similar metal suitable for cutting bone. The coil spring may be fabricated from spring steel or other metal suitable for forming springs. The retaining sleeves, plunger, and ratchet slide may be made of a polymer, although other materials may also be used. The multiple screw screwdrivers may be provided as single use tools (i.e., they may be disposable), or they may be reusable (i.e., sterilizable and/or reloadable). When supplied as a single use screwdrivers, the retaining sleeves may be fabricated in halves, with the halves of the sleeve fused together around the screwdriver shaft after the screws have been loaded onto the screwdriver shaft. The retaining sleeve may have a flange configured to mate with a groove formed on the outer surface of the screwdriver shaft if the retaining sleeve is installed in halves. This means of assembly may also allows the ratchet slide to be placed between the halves before fusing, thus facilitating fit-up of the slide within the sleeve.

Screwdriver shaft 302 may have a distal end 320 portion comprising an extended polygonal shaft 322 (obscured by screws) having a length "$L_2$" and a drilling tip 324 which may be the same as the polygonal shaft 222 and drilling tip 224 of the previously-described single screw screwdriver 200 with the exception that the length $L_2$ of polygonal shaft 322 may be longer than the length of polygonal shaft 222 of FIG. 3 so as to accommodate loading multiple screws thereon. In one embodiment, length $L_2$ may be selected in the range of from about 15 mm to about 75 mm. Proximal end 310 and polygonal proximal section 312 of the screwdriver shaft 302 may also be configured similarly to proximal end 210 and polygonal section 212 of previously-described single screw screwdriver 200 (FIGS. 2 & 3), so as to accept a driving tool, also previously discussed.

As shown in FIG. 8, the distal end 342 of transparent sleeve 340 may be tapered and may further comprise a plurality of slots 344. Slots 344 may create a plurality of segments 346 each of which may end in an axially inwardly extending lip element 348. It is these lip elements that may engage the underside 154 of flange 152 of the most distal screw 100 in the stack, thus axially retaining the screws 100 on the screwdriver shaft 302 against the biasing force of coil spring 330 (discussed below).

A coil spring 330 may be positioned over a portion of extended polygonal shaft 322 and may be used to provide a biasing force against the loaded screw stack to cause the screws to advance along the screwdriver blade once a first screw in the blade has been inserted at the surgical site. The proximal end 332 of spring element 330 may abut a shoulder region 314 of the screwdriver shaft 302, and the distal end 334 of spring element 330 may abut the head 150 of the most proximal of the stacked screws 100. Thus, when the screws are loaded onto the polygonal shaft 322, spring element 330 may be compressed between the screw stack and the shoulder region 314, axially biasing the screw stack toward the distal end of the screwdriver shaft 302. Since the screws are stacked from head to tip, the biasing force of the spring may be transferred from tip 130 of one screw 100 to head 150 of the next screw 100 of the stacked screws 100. The previously-described lips 348 may provisionally retain screws 100 within transparent sleeve 340 against the axial biasing force of coil spring 330. Thus, prior to drilling and insertion of each screw, the stack of screws is held within the retaining sleeve by lips 348.

In an alternative embodiment, instead of the segments 346 discussed in relation to FIG. 8 above, retaining sleeve 340 may have two narrow legs at the sleeve distal end 342. These legs may be configured to maintain screws 100 at the distal end of screwdriver 300, thus operating in the same manner as segments 346 and lips 348, however, these legs may not surround the screw stack. Rather, there may be sufficient space between the legs to allow increased visibility of the screw stack, which is an advantage in determining how many screws 100 may be remaining in the stack.

In operation, as the drilling tip of spring-advance multiple screw screwdriver 300 is rotated against a bone surface, a hole is drilled into the bone and screw 100 advances as described in relation to single screw screwdriver 200. As the screw 100 advances into the bone, the underside 154 of flange 152 may exert an axial force against lips 348 of retaining sleeve 340. Because the underside 154 may be sloped, the axial force applied by the underside 154 to the lips 348 may have a slight transverse component, which may cause lips 348 and associated segments 346 to be forced radially outward away from the head of the screw sufficiently to allow the screw and screw head to pass the lips 348 and exit the retaining sleeve 340. Once this screw has exited the retaining sleeve 340, the next screw 100 in line may be advanced into the most distal position on the polygonal shaft due to the bias of spring element 330, the spring element 330 causing this next screw 100 to move distally along the shaft until the underside 154 of its flange 152 rests against lips 348 of retaining sleeve 340. The device is then ready for use in applying this next screw.

Loading individual screws onto a spring-advance multiple screw screwdriver 300 may be facilitated by sliding a temporary tubular element over drilling tip 324. This tubular element further may be sized to fit within cannulation 160 of screws 100. The screws 100 may then be individually loaded over the tube and onto the extended polygonal shaft section of the screwdriver against the coil spring 330. Retaining sleeve 340 may then be placed over the tube/shaft/screws and screwed or snapped onto the screwdriver shaft, forcing the screws 100 from the tube onto the extended polygonal shaft section, and simultaneously depressing the coil spring. The tube can then be removed.

FIGS. 9-14 show an alternative embodiment of a multiple-screw loaded screwdriver according to the invention in which a ratchet mechanism, rather than the spring of the previous embodiment, is used to advance a stack of cannulated screws 100 for insertion into bone. Ratchet-advance multiple screw screwdriver 400 may comprise a stacked screwdriver blade 402, a plunger 450, a screw retaining sleeve 460, and a ratchet slide 470. In this embodiment, a finger-operated ratchet mechanism may act in association with the plunger 450 to allow the user to manually advance a pre-loaded stack of screws 100 to advance the screws 100 as desired. Screw-retaining sleeve 460 may include a mechanism similar to that described in relation to the spring-loaded embodiment of the multiple-screw screwdriver 300 from prematurely detaching from the distal end of the screwdriver blade 402.

The stacked screw driver blade 402 itself may be exactly the same as the blade described in relation to stacked screw driver blade 302 of spring-advance multiple screw screwdriver 300, and thus blade 402 may have an extended polygonal shaft 422 having a length "$L_3$, and a drilling tip 424. The polygonal shaft 422 and drilling tip 424 may be the same as the shaft and tip described in relation to polygonal shaft 222 and drilling tip 224 of single screw screwdriver 200 (FIGS. 2 & 3). The length $L_3$ of polygonal shaft 422, however, may be longer than the length of shaft 222 of FIG. 3 so as to accommodate loading multiple screws thereon. As such, length $L_3$ may be selected in the range of from about 15 mm to about 75 mm. Proximal end 410 and polygonal proximal section 412 of the screwdriver shaft 402 may also be configured similarly to proximal end 210 and polygonal section 212 of single screw screwdriver 200 (FIGS. 2 & 3), to accept a driving tool as previously discussed.

Figure 13:
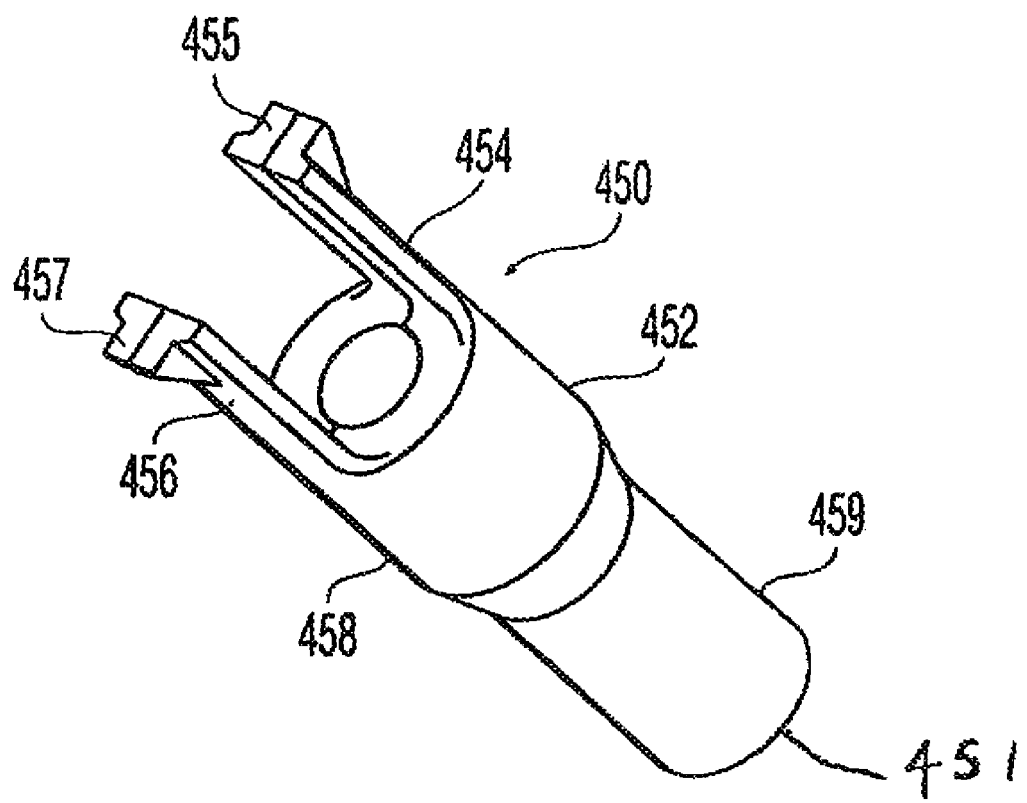
FIG. 13 is a detail view of the plunger of the multiple screw screwdriver of FIG. 9.
Figure 14:
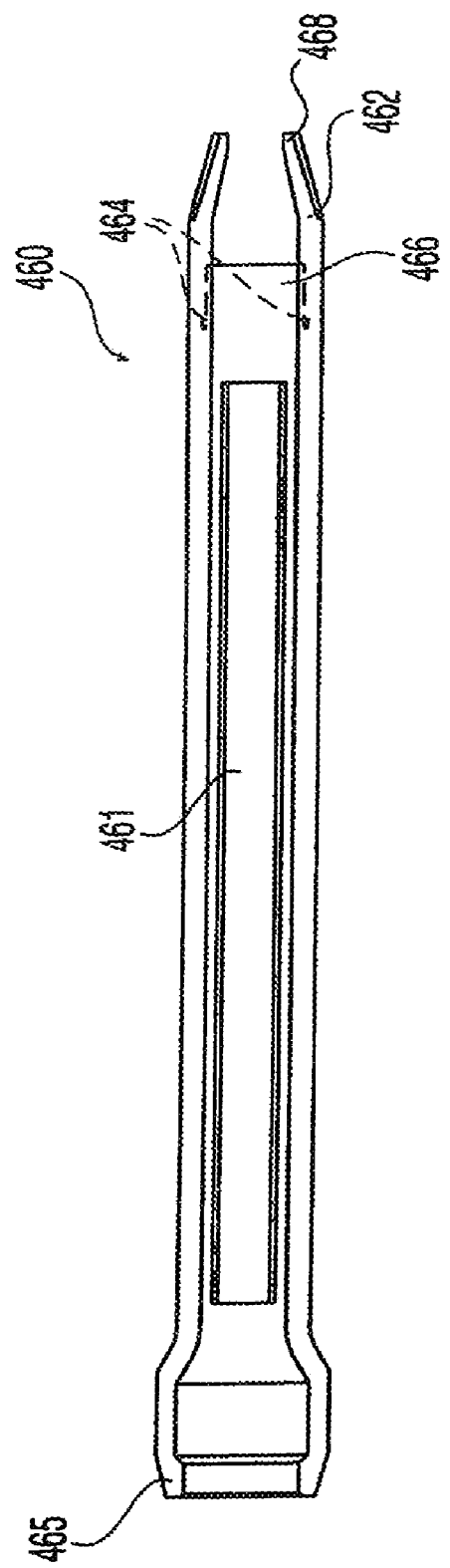
FIG. 14 is a section of the retaining sleeve of the multiple screw screwdriver of FIG. 9.

As shown in FIG. 13, plunger 450 may comprise a cannulated cylinder portion 452 and two axially extending legs 454, 456. Each leg 454, 456 may further comprise a triangular shaped ratchet tab 455, 457 which may protrude radially from the proximal end of its respective leg 454, 456. The cylinder portion 452 of the plunger 450 may be sized to slide within an annular region 480 formed between retaining sleeve 460 and the polygonal section 422 of the screwdriver blade 402. The cylinder portion 452 of plunger 450 may further have a larger diameter proximal section 458 having a first diameter, and a distal section 459, having a second diameter. The first diameter may be greater than the second diameter, the first diameter section 458 sized to slide within the retaining sleeve 460, and the second diameter section 459 having a distal end face 451 sized to axially engage the head portion of the most proximal of the screws 100 in the stack.

FIGS. 11 and 12 provide details of ratchet slide 470, which may comprise a pair of longitudinal grooves 472, 474 which may be disposed on either side of the slide 470, a plurality of evenly spaced depressions 476 located on the bottom surface of the slide 470, and a knurled raised surface 478 located on the top surface of the slide suitable for gripping the slide 470 to apply an axial force to the top of the slide 470. Longitudinal grooves 472, 474 are sized and configured to slide within a longitudinal ratchet slide slot 461 disposed in the retaining sleeve 460. Ratchet slide slot 461 may extend along a substantial portion of the length of retaining sleeve 460, thus allowing the user to move the ratchet slide 470 axially along a substantial portion of the sleeve 460. Likewise, the ratchet slide slot 461 may have a width configured to allow the sides of the ratchet slide slot 461 to engage grooves 472, 474 while allowing the ratchet slide 470 to slide easily within the slot 461 in the sleeve 460. In an alternative embodiment, the sides of the ratchet slide slot 461 could comprise grooves and the sides of ratchet slide 470 could be slidably received within the grooves 472, 474.

As illustrated in FIG. 11, each ratchet depression 476 may form a right triangle when viewed from the side, the depression having a substantially perpendicular surface 477 located at the proximal end of the depression. The ratchet depressions 476 may be configured to receive one of the triangular shaped ratchet tabs 455, 457 of plunger 450 (FIG. 13) when the device is assembled. The depressions 476 may be provided at regularly-spaced intervals along the bottom surface of the slide 470, and the distance between depressions 476 may be approximately the length of a single screw 100. Alternatively, the distance between depressions may be variable, such as to accommodate screws of different diameters placed within the stack.

Figure 10:
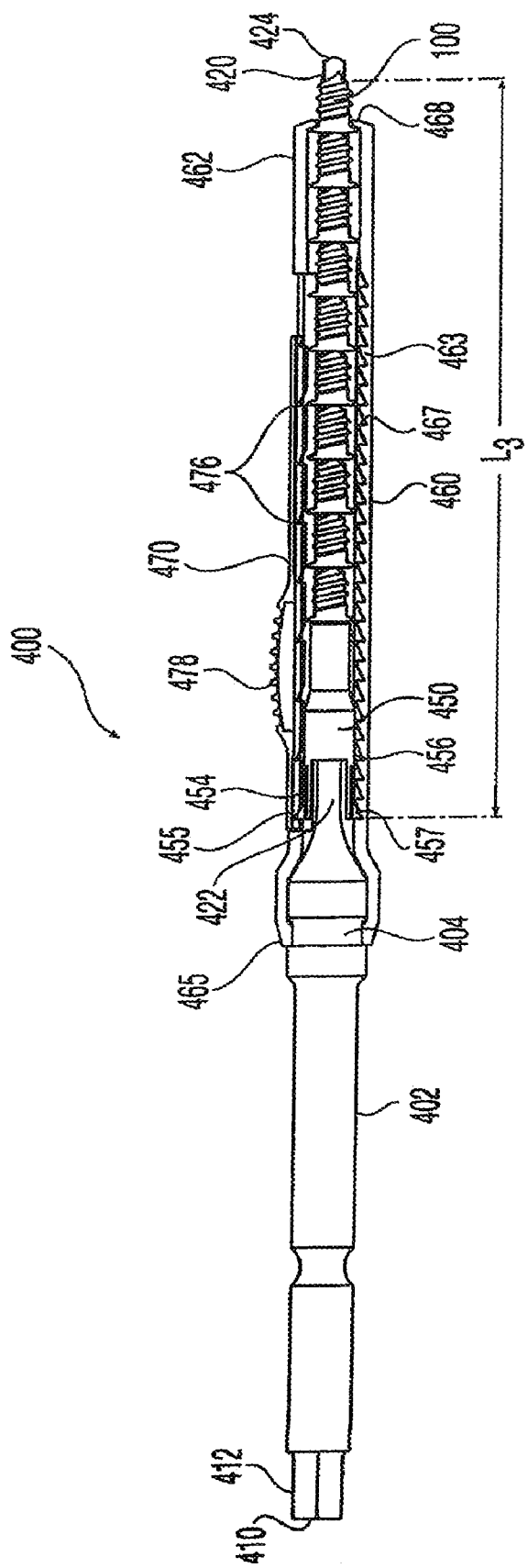
FIG. 10 is cross-sectional view of the multiple screw screwdriver of FIG. 9.

As illustrated in FIG. 10, the inner surface of retaining sleeve 460 may include a series of similar evenly spaced right triangular shaped depressions 463 disposed approximately 180° about the circumference of the retaining sleeve from ratchet slide slot 461. The ratchet depressions 463 may each have a substantially perpendicular surface 467 located at the proximal end of each depression 463, and the depressions 463 may be configured to receive one of tabs 455, 457 of plunger 450 when the device is assembled. The depressions 463 may be provided at regularly-spaced intervals along the inner surface of the retaining sleeve 460, and the distance between depressions 463 may be less than, greater than, or approximately equal to the distance between the depressions 476 of slide 470.

As with spring-advance multiple screw screwdriver 300, screws 100 of ratchet-advance multiple screw screwdriver 400 may occupy the annular space between extended polygonal shaft section 422 (obscured by screws) and retaining sleeve 460. The loaded screws 100 may be advanced for use by grasping knurled raised surface 478 and sliding ratchet slide 470 within ratchet slide slot 461 of retaining sleeve 460 in the distal direction.

The lengths of ratchet slide slot 461 and ratchet slide 470 may be such that ratchet slide 470 can slide only approximately the length of one screw 100. Thus, to operate the device the ratchet slide 470 may be moved distally within the slot 461 to advance the screw stack by a single screw length, thus positioning a new screw at the distal end of the screwdriver. The slide 470 may subsequently be moved in the proximal direction which may return the slide 470 to its original unactuated position. This movement may then be repeated until all of the screws in the stack have been used. Note that although the depressions and tabs are shown and described as triangular, any shape that results in a ratchet action with reciprocating movement of the parts is anticipated. For example, the tabs and depressions could have corresponding curved surfaces, or other appropriate surfaces that would be apparent to one of ordinary skill in the art.

The initial position of the ratchet slide 470, plunger 450, retaining sleeve 460, and screws 100 is shown in FIG. 10. As previously described, screws may be advanced toward the distal end of the screwdriver by gripping the knurled raised surface 478 and moving the ratchet slide 470 axially in the distal direction. The right angle side 477 of one of the depressions in ratchet slide 470 may engage a similar perpendicular surface of matching tab 455 of plunger leg 454, thus forcing plunger 450 to move axially with ratchet slide 470. This axial movement may force ratchet tab 457 on leg 456 out of depression 463 in retaining sleeve 460. Due to the respective acute angles of the mating surfaces of tab 457 and depression 463, leg 456 may flex radially inward, allowing plunger 450 to slide within axially in the distal direction within retaining sleeve 460. When ratchet slide 470 is subsequently returned to the proximal end of ratchet slide slot 461, the relative motions between tabs 455, 457 on legs 454, 456 of plunger 450 and depressions 463 in retaining sleeve 460 and depressions 476 in ratchet slide 470 are reversed (i.e., the respective perpendicular surfaces plunger leg 457 and depressions 463 engage and the respective acute angles of the mating surfaces of tab 455 and ratchet depressions 476 may cause leg 454 to flex outward), thus causing plunger 450 to remain in place within retaining sleeve 460. With each distal ratcheting movement (i.e., actuation) of the ratchet slide, the smaller diameter section 459 of plunger 450 applies an axial force to the upper flange 156 of the most proximal of the loaded screws, thus moving the entire stack as described in relation to the spring-loaded embodiment. Thus, the larger diameter section 458 of plunger 450 may provide a close sliding fit with the inner surface of retaining sleeve 460, while the smaller diameter section 459 may be sized to allow plunger 450 to push the last screw 100 into position without forcing segments 466 (FIG. 14) apart and allowing the last screw 100 to become prematurely detached from screwdriver 400.

Ratchet-advance multiple screw screwdriver 400 may be loaded by sliding plunger 450 onto the extended polygonal shaft section 422 followed by screws 100. Retaining sleeve 460—with ratchet slide 470 already mounted—may then be slid over screws 100 and plunger 450 (with legs 454, 456 and ratchet tabs 455, 457 of plunger 450 aligned with ratchet depressions 463 in retaining sleeve 460 and ratchet depressions 476 in ratchet slide 470) and snapped into place, with flange 465 of retaining sleeve 460 engaging groove 404 of screwdriver shaft 402. It should be noted that other means of attaching retaining sleeve 460 to screwdriver shaft 402 may be used such as set screws or any other means of attachment well-known in the art.

Additionally, screwdriver shaft 402, plunger 450, and retaining sleeve 460 may all comprise corresponding keyed surfaces so that the components can only be assembled in the proper orientation (i.e., with depressions 463 and 476 aligned with legs 454, 456). Ratchet slide 470 may be snapped into place within ratchet slide slot 461 due to the flexibility of the material of construction of retaining sleeve 460 and/or ratchet slide 470. Alternatively, retaining sleeve 460 may be fabricated in two parts and assembled after ratchet slide 470 is slid into an open ended ratchet slide slot 461.

In use, the screwdriver may be provided having one or more screws 100 pre-loaded onto the shaft of the screwdriver. The pointed end of the flat blade portion of the screwdriver may then be applied to a targeted site on a bone surface. As the screwdriver is rotated and the flat blade portion bores into the bone surface, the screwdriver is advanced into the bone. The cutting flutes of screw 100 may then begin to also cut into the bone. Once the blade and screw have advanced into the bone a distance sufficient to cause engagement of the screw threads with the bone, further rotation of the blade may cause the screw 100 to move off the blade as the screw tunnels into the bone. When the multiple-screw screwdriver is used, this axial movement of the screw 100 in relation to the screwdriver may also cause the screw to pull axially away from the retaining sleeve, freeing the screw from the sleeve and allowing the next screw 100 in the stack to advance to the distal end of the screwdriver, either via the force of spring 300, or the ratcheting movement of ratchet slide 470.

The cannulated screw system of the present invention may be provided as a kit including a single screw screwdriver and/or one or more multiple screw screwdrivers, a plurality of cannulated screws, and optionally one or more bone plates. For the multiple screw screwdrivers, screws may be provided preloaded onto the screwdriver shaft, or they may be provided separately. Where plates are provided as part of the kit, the plates may be provided in a variety of different materials, such as stainless steel, titanium, polymer, or bioresorbable materials. Although a wide variety of uses for the invention are contemplated, the cannulated screw system is particularly applicable to use on fractures of the face and skull. The low profile screws are particularly useful for avoiding screw-head protrusions when the screws are used in areas of the head in which there is little flesh (fat, muscle, etc.) covering the bone surface. Furthermore, the screws and/or plates may be bioresorbable, which may eliminate the need to make additional incisions to remove these fixation elements once healing is complete.

Further, it should be understood that variations and modifications within the spirit and scope of the invention may occur to those skilled in the art to which the invention pertains. Accordingly, all expedient modifications readily attainable by one versed in the art from the disclosure set forth, herein that are within the scope and spirit of the present invention are to be included as further embodiments of the present invention. The scope of the present invention is accordingly defined as set forth in the appended claims.

What is claimed is:

1. A method of installing a bone screw in bone, comprising:
   providing at least a first screw and a second screw, each screw comprising a cannulation;
   providing a screwdriver comprising a first end and a second end, a drilling blade disposed on the first end, and a shaft shaped to rotationally engage the cannulations of at least the first screw and the second screw;

rotationally engaging the cannulations of at least the first screw and the second screw with the shaft of the screwdriver;

rotating the drilling blade of the screwdriver against the surface of a bone;

continuing rotation of the drilling blade until the first screw is fully engaged in the bone; and removing the screwdriver from the cannulation of the first screw after the first screw is securely engaged in the bone while retaining the second screw.

2. The method of claim 1, wherein the screw has a head portion, said head portion comprising a flange having an underside configured to engage a bone or bone plate surface.

3. The method of claim 1, wherein the screw has at least one cutting flute for engaging and cutting bone.

4. The method of claim 1, wherein the screwdriver is disposable.

5. The method of claim 1, wherein the screwdriver is reusable.

6. The method of claim 1, wherein the screwdriver further comprises a shoulder on the shaft and a spring having a first end configured to engage the shoulder and a second end configured to engage the head portion of the first screw, the spring further configured to bias the first screw toward the first end of the screwdriver.

7. The method of claim 6, wherein the screwdriver further comprises a sleeve that provisionally axially retains the screws to the screwdriver.

8. The method of claim 7, wherein the sleeve is transparent.

9. The method of claim 7, wherein the sleeve has a lip to maintain the screws until inserted into the bone.

10. The method of claim 1, wherein the sleeve further comprises legs configured to provisionally axially retain the screws to the screwdriver.

11. The method of claim 1, wherein the screwdriver has a ratchet system, the ratchet system comprising a sliding member with depressions or protrusions, a sleeve surrounding the intermediate portion of the screwdriver with depressions or protrusions, and a plunger with leg members that engage the depressions or protrusions of the sliding member and sleeve member, wherein the sleeve member has a slot within which the sliding member slides so as to advance the screws for insertion into the bone.

12. The method of claim 11, wherein the sleeve has a lip disposed at one end, the lip configured to provisionally axially retain the screws to the screwdriver.

13. The method of claim 11, wherein the sleeve further comprises legs configured to provisionally axially retain the screws to the screwdriver, the legs further configured to allow visualization of screws within the sleeve.

* * * * *

UNITED STATES PATENT AND TRADEMARK OFFICE
CERTIFICATE OF CORRECTION

PATENT NO. : 7,766,920 B2
APPLICATION NO. : 10/988253
DATED : August 3, 2010
INVENTOR(S) : Paul Ciccone et al.

It is certified that error appears in the above-identified patent and that said Letters Patent is hereby corrected as shown below:

Column 5,
Line 20, delete "αmay" and insert -- α may --.
Line 21, delete "αmay" and insert -- α may --.

Signed and Sealed this

Twelfth Day of October, 2010

David J. Kappos
*Director of the United States Patent and Trademark Office*